United States Patent [19]
Wenstrom, Jr.

[11] Patent Number: 5,860,983
[45] Date of Patent: Jan. 19, 1999

[54] BONE ANCHOR INSERTER, METHOD FOR LOADING SAME, METHOD FOR HOLDING AND DELIVERING A BONE ANCHOR, AND METHOD FOR INSERTING A BONE ANCHOR IN A BONE

[75] Inventor: Richard F. Wenstrom, Jr., Norwood, Mass.

[73] Assignee: Mitek Surgical Products, Inc., Westwood, Mass.

[21] Appl. No.: 921,831

[22] Filed: Sep. 2, 1997

Related U.S. Application Data

[62] Division of Ser. No. 589,137, Jan. 19, 1996, Pat. No. 5,662,658.

[51] Int. Cl.⁶ .................................................... A61B 17/58

[52] U.S. Cl. ............................. 606/104; 606/72; 606/232

[58] Field of Search .................................... 606/104, 232, 606/139, 144, 72; 227/179.1, 175.1; 81/463

[56] References Cited

U.S. PATENT DOCUMENTS

| | | | |
|---|---|---|---|
| 5,466,243 | 11/1995 | Schmieding et al. | 606/104 |
| 5,628,751 | 5/1997 | Sander et al. | 606/104 |

*Primary Examiner*—Michael Powell Buiz
*Assistant Examiner*—Julian W. Woo
*Attorney, Agent, or Firm*—Pandiscio & Pandiscio

[57] ABSTRACT

A bone anchor inserter for insertion of a bone anchor into a bore in a bone, the inserter comprising a handle having a grip portion, an actuator member mounted on the handle, a sleeve fixed in the handle and extending therefrom, and a shaft fixed at one end to the actuator member and slidably movable in the sleeve. The sleeve is provided with an opening in a side wall thereof proximate, but spaced from, a free end of the sleeve. The opening facilitates loading a bone anchor therethrough and into the sleeve between a free end of the sleeve and a distal end of the shaft. The invention further contemplates a method for loading a bone anchor inserter, a method for holding and delivering a bone anchor, and a method for inserting a bone anchor in a bore in a bone.

3 Claims, 5 Drawing Sheets

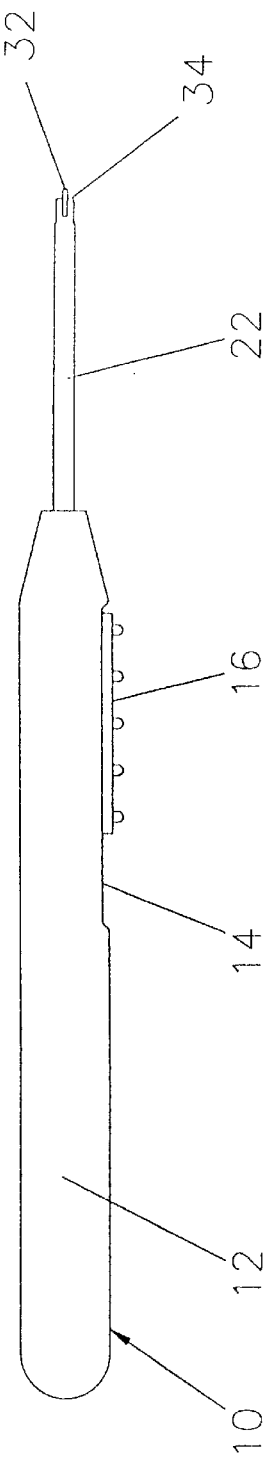
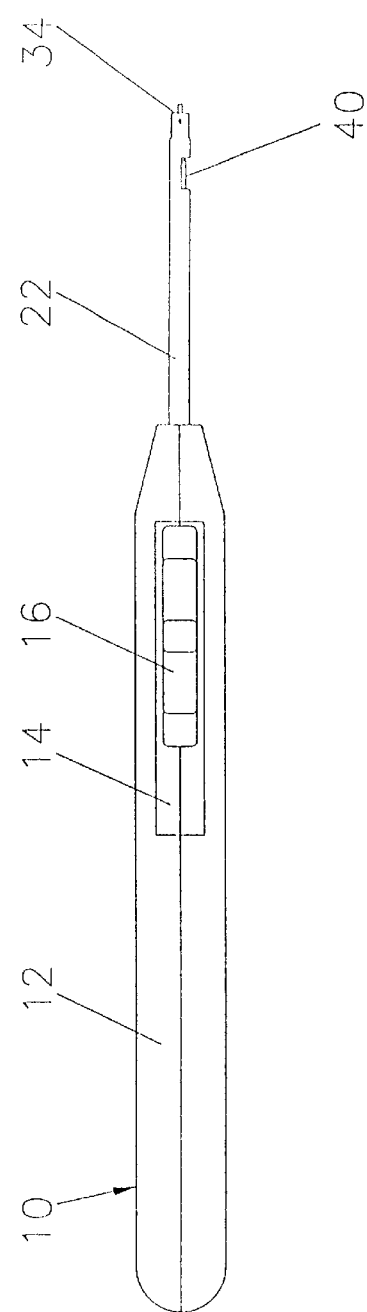
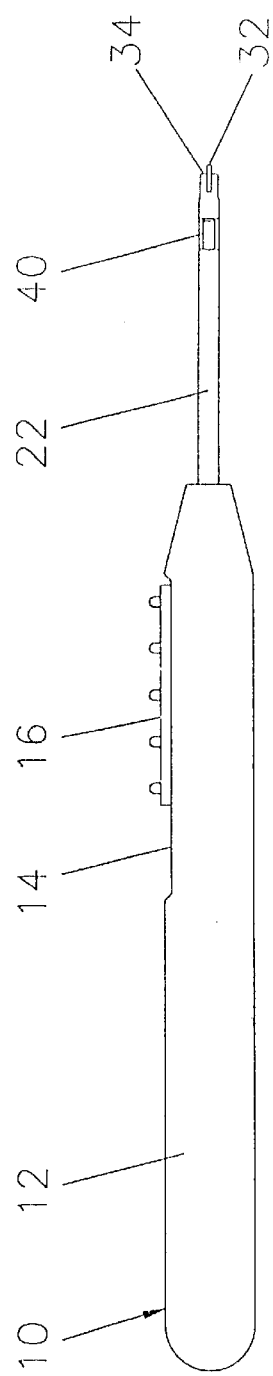
FIG. 3
FIG. 1
FIG. 2

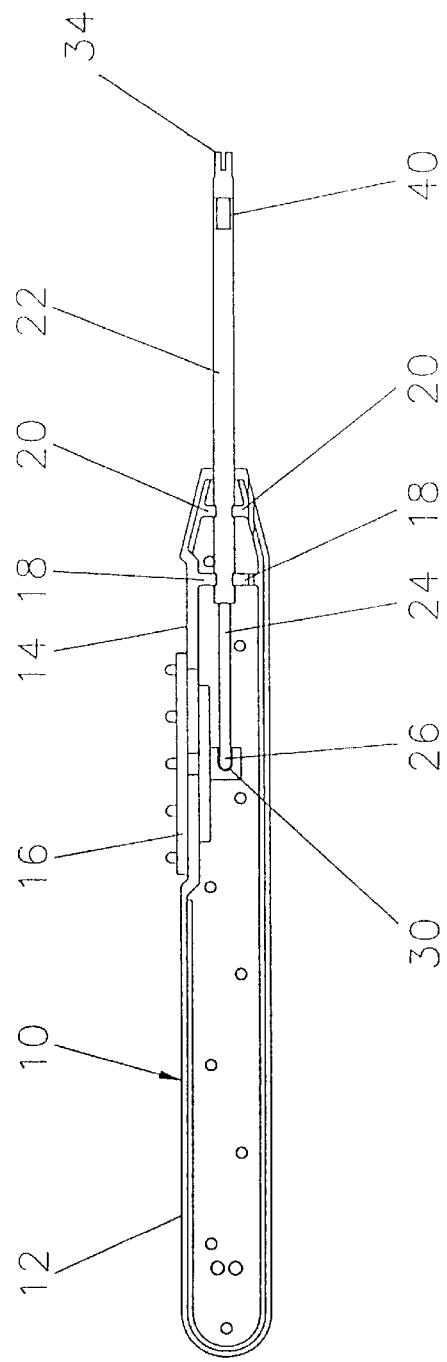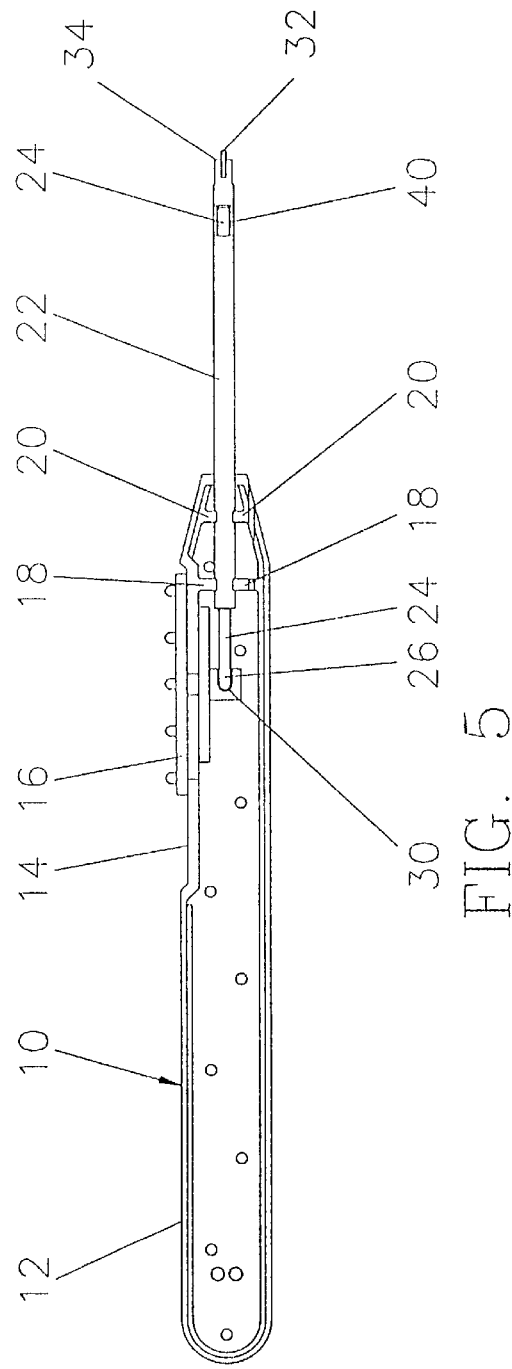

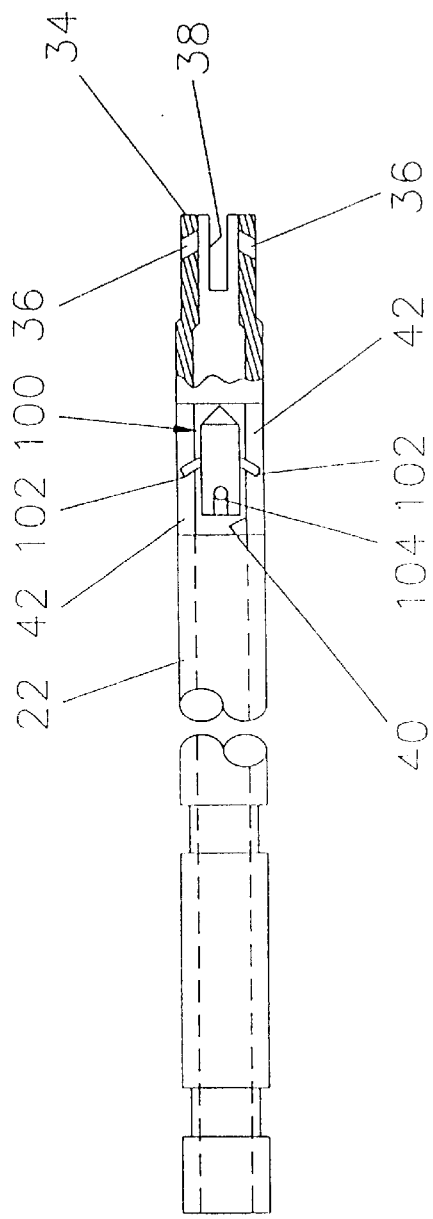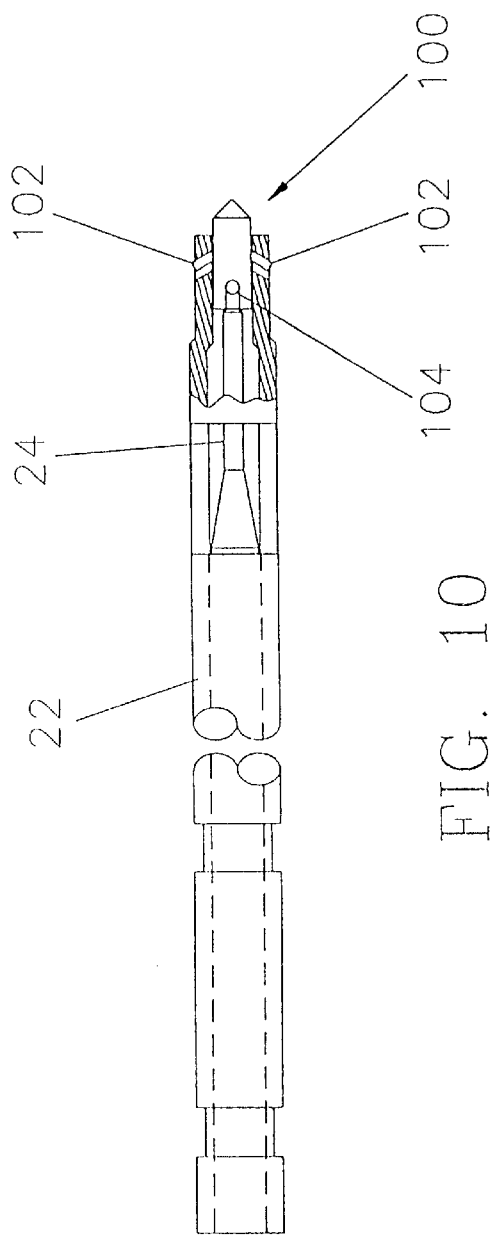

5,860,983

BONE ANCHOR INSERTER, METHOD FOR LOADING SAME, METHOD FOR HOLDING AND DELIVERING A BONE ANCHOR, AND METHOD FOR INSERTING A BONE ANCHOR IN A BONE

This is a division of U.S. patent application Ser. No. 08/589,137 filed Jan. 19, 1996 now U.S. Pat. No. 5,662,658 by Richard F. Wenstrom, Jr. for BONE ANCHOR INSERTER, METHOD FOR LOADING SAME, METHOD FOR HOLDING AND DELIVERING A BONE ANCHOR, AND METHOD FOR INSERTING A BONE ANCHOR IN A BONE.

FIELD OF THE INVENTION

This invention relates to surgical instruments in general, and more particularly to an inserter assembly for inserting a bone anchor in a bore in a bone, a method for loading same, a method for holding and delivering a bone anchor, and a method for inserting a bone anchor in a bone.

BACKGROUND OF THE INVENTION

Bone anchors for attaching suture, bone and/or tissue to bone are well known in the art. Also well known are inserter tools for deploying such bone anchors in bone. Examples of such devices may be seen in U.S. Pat. Nos. 4,898,156; 4,899,743; 4,946,468; 4,968,315; 5,002,550; 5,046,513; 5,192,303; 5,207,679; and 5,217,486; and in U.S. patent applications Ser. Nos. 07/981,011; 08/030,657; 08/075,168; 08/098,599; 08/180,425; 08/197,927; and 08/312,892.

While the bone anchor inserter tools disclosed in the foregoing U.S. patents and patent applications have proven satisfactory, it has been noted that certain problems arise from time to time when using such tools.

More particularly, the bone anchor inserters of the prior art typically include a sleeve open at a distal end. In loading an anchor into the sleeve, the anchor is pushed through the open end of the sleeve and into the sleeve. See, for example, the above-identified U.S. patent application Ser. No. 08/312,892. Given the small dimensions of the anchors and sleeves involved, it is sometimes difficult to obtain the correct alignment of anchor and sleeve. Instead of the anchor being readily slipped into the sleeve, the anchor sometimes slips away and falls from the hand. Compounding the difficulty in some devices is the fact that many anchors are provided with barbs or the like. The barbs extend outwardly from the device and are pointed in such direction as to resist insertion into the open end of a sleeve.

In the above-identified U.S. patent application Ser. No. 08/312,894, there is disclosed an alternative loading arrangement wherein the anchor is inserted in a proximal end of a shaft. The shaft is discrete from the remainder of the inserter assembly. With the anchor in the shaft, the shaft is connected to the inserter assembly.

There is a need, in bone anchor inserters, for an easier and more reliable anchor loading facility. More particularly, there is a need for a bone anchor loading facility wherein an anchor may be readily loaded into an inserter shaft without having to disassemble and reassemble the inserter. There is further needed an improved method for loading a bone anchor into a bone anchor inserter, an improved method for holding and delivering a bone anchor, and an improved method for inserting a bone anchor in a bore in a bone.

OBJECTS OF THE INVENTION

Accordingly, one object of the invention is to provide an improved bone anchor inserter having means for effecting quick and easy loading of the inserter with a bone anchor.

A further object of the invention is to provide an improved method for loading a bone anchor into a bone anchor inserter.

A still further object of the invention is to provide an improved method for holding and delivering a bone anchor.

A still further object of the invention is to provide an improved method for inserting a bone anchor in a bore in a bone.

SUMMARY OF THE INVENTION

These and other objects of the present invention are addressed by the provision and use of a novel bone anchor inserter comprising a handle having a grip portion. An actuator member is mounted on the handle. A sleeve is fixed to the handle and extends therefrom. A shaft is fixed at a first end to the actuator member and is slidably movable in the sleeve. The sleeve is provided with an opening in a side wall thereof proximate to, but removed from, a free end of the sleeve. The opening facilitates insertion of a bone anchor therethrough and into the sleeve between the free end of the sleeve and a second end of the shaft.

In accordance with a further feature of the invention, there is provided a method for loading a bone anchor into a bone anchor inserter. The method comprises providing an inserter having a handle, a sleeve extending from the handle and having an opening in a side wall thereof, a shaft slidably disposed in the sleeve, and an actuator operative from the handle to move the shaft axially in the sleeve. The method includes the further steps of manipulating the actuator to move the shaft in the sleeve so as to move a distal end of the shaft proximally of the opening, inserting a bone anchor through the opening and into the sleeve, and manipulating the actuator to move the shaft in the sleeve so as to engage the anchor and move the anchor in the sleeve to a position distally of the opening and then proximally of a sleeve distal end.

In accordance with a still further feature of the invention, there is provided a method for holding and delivering a bone anchor. The method comprises providing a bone anchor inserter having a handle, a sleeve extending from the handle and having an opening in a side wall thereof, a shaft slidably disposed in the sleeve, and an actuator operative from the handle to move the shaft axially in the sleeve. The method includes the further steps of inserting a bone anchor through the opening and into the sleeve, and manipulating the actuator to move the shaft to engage the anchor in the sleeve so as to move the anchor out a free end of the sleeve.

In accordance with a still further feature of the invention, there is provided a method for inserting a bone anchor in a bore in a bone. The method comprises providing a bone anchor inserter including a handle, a sleeve extending from the handle and having an opening in a side wall thereof, a shaft slidably disposed in the sleeve, and an actuator operative from the handle to move the shaft axially in the sleeve. The method includes the further steps of inserting a bone anchor through the opening and into the sleeve, aligning a free end of the sleeve with the bore, and manipulating the actuator to move the shaft to engage the anchor in the sleeve so as to move the anchor out a free end of the sleeve and into the bore.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 1 is a top plan view of an inserter formed in accordance with the present invention;

FIG. 2 is a right side elevational view of the inserter of FIG. 1;

FIG. 3 is a left side elevational view of the inserter of FIG. 1;

FIG. 4 is a right side elevational view of the inserter of FIG. 2, but with a handle portion removed to reveal the interior of the handle and the components therein in a first operative position;

FIG. 5 is a view similar to that of FIG. 4, but with components within the handle in a second operative position;

FIG. 9 is a side elevational view, in part in section, showing a bone anchor being placed in the opening in the sleeve whereby the anchor may be loaded into the interior of the sleeve; and FIG. 10 is a side elevational view, in part in section, showing a bone anchor disposed in the sleeve component of the inserter, with the inserter's shaft component having moved the bone anchor toward the distal end of the sleeve so that the anchor's barbs are positioned in holes appropriately formed in the sleeve.

DETAILED DESCRIPTION OF THE PREFERRED EMBODIMENT

Figure 6:
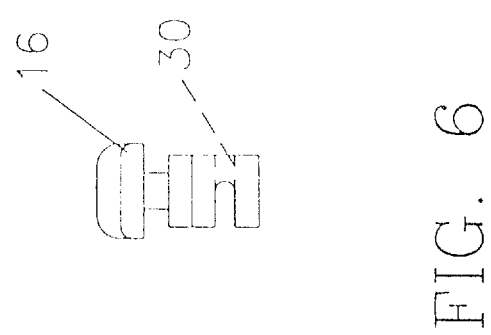
FIG. 6 is a front view of an actuator member mounted on the handle.

Referring to FIGS. 1–5, it will be seen that the illustrative inserter includes a handle 10 having a grip portion 12. The inserter further includes an actuator member mounting portion 14, and an actuator member 16 mounted on the actuator member mounting portion 14.

Handle 10 is further provided with sleeve mounting portions 18, 20 (FIGS. 4 and 5) comprising rib means extending inwardly from the shell of handle 10, which preferably is made of a molded rigid plastic material.

Figure 8:
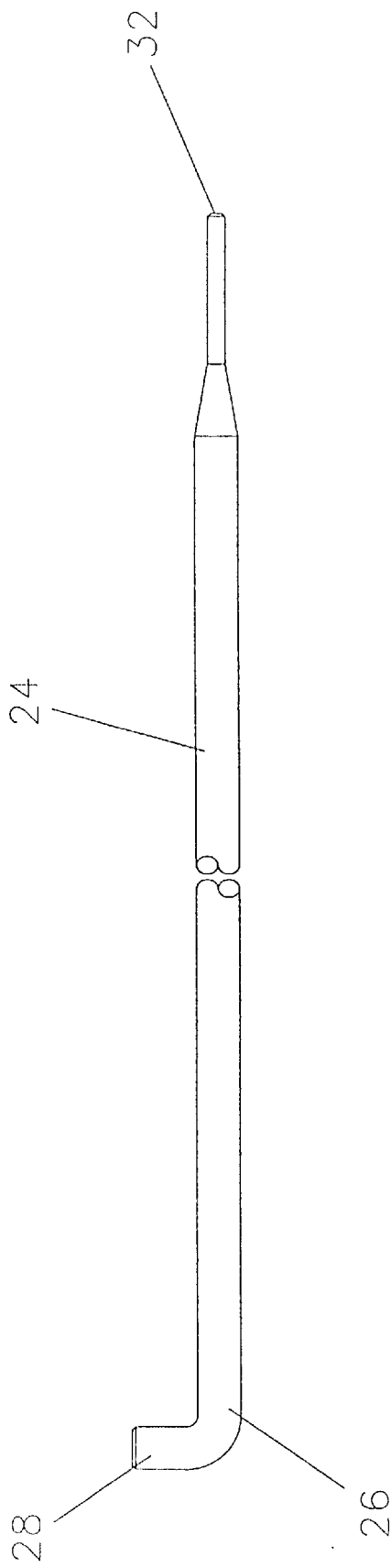
FIG. 8 is a top plan view of a shaft component of the inserter.

The inserter further comprises a sleeve 22 fixed to sleeve mounting portions 18, 20 and retained thereby in a stationary manner. Sleeve 22 preferably is made of stainless steel. A shaft 24, preferably also made of stainless steel, is slidably disposed within sleeve 22. At a first end 26 thereof, shaft 24 is provided with a hook portion 28 (FIG. 8) which is disposed in a bore 30 (FIG. 6) of actuator 16, so as to connect first end 26 of shaft 24 to actuator 16 (FIG. 4).

Referring still to FIGS. 4 and 5, it will be seen that when actuator 16 is in a rearward-most (i.e., leftward-most in FIG. 4) position, a second end 32 of shaft 24 is retracted well into sleeve 22, removed from a free end 34 of sleeve 22; and when actuator 16 is in a forward-most position (i.e, rightward-most in FIG. 5), second end 32 of shaft 24 extends outwardly from free end 34 of sleeve 22.

While many embodiments of actuator member 16 may suit the purpose, it has been found that actuator member 16 may most appropriately comprise a thumb-activated slide member and the actuator member mounting portion 14 may comprise a slide member mounting portion, as shown in the drawings.

Figure 7:
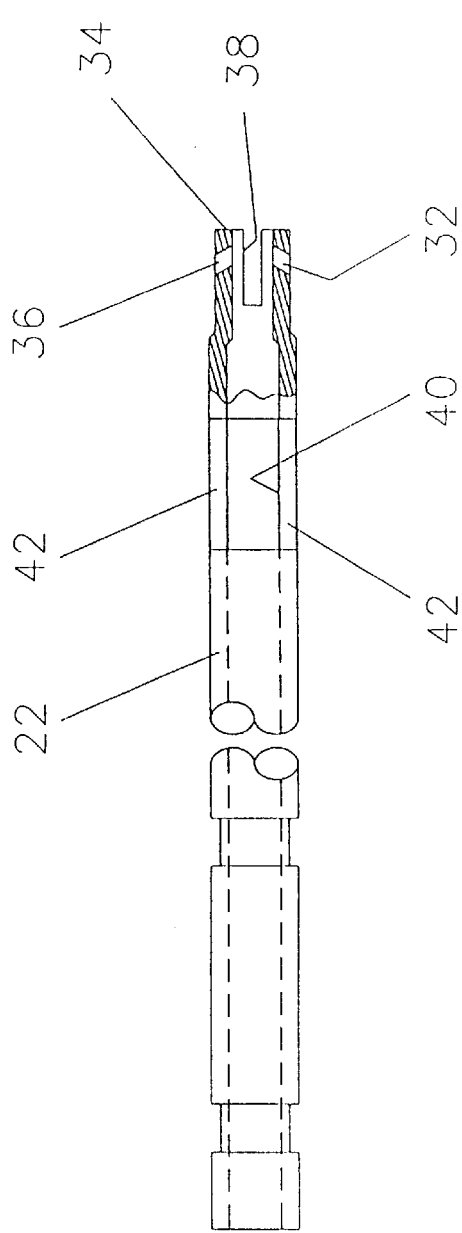
FIG. 7 is a side elevational view, in part in section, showing a sleeve component of the inserter.

Referring to FIG. 7, it will be seen that sleeve 22 is provided, near its free end 34, with an opposed pair of holes 36 and an opposed pair of open-ended slots 38 (only one of which is shown in FIG. 7). Holes 36 are for receiving bone anchor barbs and slots 38 are for receiving a strand of suture, as is taught in the aforementioned U.S. patent application Ser. No. 08/312,894, which is incorporated herein by reference.

Referring to FIGS. 1–5 and 7, it will be seen that sleeve 22 is further provided, proximate to but removed from free end 34 thereof, with an opening 40 in a side wall of the sleeve. Preferably, opening 40 is of a rectangular configuration and is sized such that an anchor may be passed therethrough. That is, rather than loading an anchor into the open end of shaft 22, an anchor is simply inserted through opening 40 into the shaft. The opening preferably occupies no more than 180° of the circumference of sleeve 22, so that the anchor receiving portion of the sleeve underlying the opening is cup-shaped and well adapted to receive and retain an anchor passed through the opening. Further, the 180° opening is such that barbs extending outwardly from the anchor in diametrically opposite directions may be rested upon lengthwise side edges 42 (FIG. 7) of the slot. To this end, the axially extending side edges 42 of the opening 40 preferably are disposed in the same plane. Thus, the opening 40 may simply be cut from the sleeve 22 without machining of radially-extending surfaces.

Opening 40 is spaced from free end 34 of sleeve 22 a distance at least equal to, and usually exceeding, the length of the opening 40. The length of opening 40 is, in turn, dictated by the length of the anchor which is to be used in conjunction with the inserter. In one embodiment, for example, opening 40 is about 0.165–0.185 inch and is spaced from free end 34 of sleeve 22 by about 0.250 inch. Thus, an anchor may be introduced into sleeve 22, moved free of the opening 40, and moved into the area having barb receiving holes 36 (FIG. 7) and suture receiving slots 38. It will be apparent, however, that dimensional features for each inserter depend primarily upon the size of the bone anchor contemplated.

In operation, inserter handle grip portion 12 is grasped in one hand by an operator such that a thumb is free to engage actuator 16. If shaft 24 is not in a retracted position, the operator moves actuator 16 rearwardly to move second end 32 of shaft 24 rearwardly, or proximally, of opening 40. A bone anchor is then inserted into sleeve 22 through opening 40. The anchor is placed in opening 40 such that barbs extending from the anchor, shown and discussed in the aforementioned U.S. patent application Ser. No. 08/312,894, rest upon side edges 42 of opening 40. See, for example, FIG. 9, which shows a bone anchor 100 placed in the sleeve opening 40 such that the anchor's barbs 102 rest upon side edges 42.

Using actuator 16, the operator moves shaft 24 forwardly to engage the anchor and move the anchor forwardly in sleeve 22. The anchor is moved forwardly, or distally, until the aforementioned barbs on the anchor engage holes 36 in sleeve 22. To accommodate receipt of the anchor barbs, holes 36 are aligned with side edges 42 of opening 40. Once the barbs have entered holes 36, the anchor is thereby securely retained in sleeve 22. See, for example, FIG. 10, which shows the bone anchor 100 disposed in the distal end of sleeve 22, with the bone anchor's barbs 102 located in sleeve holes 36, and with the bone anchor's suture-receiving opening 104 aligned with the sleeve's slots 38. It is to be appreciated that holes 36 are formed so that when the anchor's barbs are disposed in holes 36, the barbs will not be deformed and the anchor will be very securely seated in sleeve 22. When it is desired to use the anchor to attach suture to a bone, a suture strand is fed through one of the slots 38 in sleeve 22, through the opening 104 in the bone anchor, and out the opposite slot 38, as is fully disclosed in the above-referenced U.S. patent application Ser. No. 08/312,894. Inasmuch as the bone anchor opening is typically disposed rearwardly of the bone anchor barbs, slots 38 extend well rearwardly in sleeve 22 beyond holes 36. At this point, the inserter is in condition to deploy the anchor in a bone prepared with an appropriate bore therein.

To effect deployment of the anchor, second end 34 of sleeve 22 is positioned at the mouth of the bore in the bone (not shown herein but shown and described in the aforementioned U.S. patent application Ser. No. 08/312,894). The operator moves actuator 16 forwardly, which causes shaft 24, connected thereto, to move forwardly. Second end 32 of shaft 24 pushes the anchor out of the open end of sleeve 22 and into the bore in the bone. Shaft 24 extends outwardly from free end 34 of sleeve 22 (FIG. 5) to move the anchor well into the bone bore.

Thus, there is provided a bone anchor inserter having means by which the inserter may easily be loaded with a bone anchor and in which the loading opening can remain in view of the operator, even when the inserter is in an operative attitude. There is further provided an improved method for loading a bone anchor inserter, an improved method for holding and delivering a bone anchor, and an improved method for inserting a bone anchor in a bone.

It is to be understood that the present invention is by no means limited to the particular construction herein disclosed and/or shown in the drawings, but also comprises any modification or equivalents within the scope of the claims.

What is claimed is:

1. A method for loading a bone anchor into a bone anchor inserter, the method comprising the steps of:

providing an inserter comprising:
a handle;
a sleeve extending from said handle and having an opening in a side wall thereof;
a shaft slidably disposed in said sleeve; and
an actuator operative from said handle to move said shaft axially in said sleeve;

manipulating said actuator to move said shaft in said sleeve to move a distal end of said shaft proximally of said opening;

inserting a bone anchor through said opening and into said sleeve; and manipulating said actuator to move said shaft in said sleeve to engage said anchor and move said anchor in said sleeve to a position distally of said opening and proximally of a sleeve distal end.

2. A method for holding and delivering a bone anchor, the method comprising the steps of:

providing a bone anchor inserter comprising:
a handle;
a sleeve extending from said handle and having an opening in a side wall thereof;
a shaft slidably disposed in said sleeve; and
an actuator operative from said handle to move said shaft axially in said sleeve;

inserting a bone anchor through said opening and into said sleeve; and manipulating said actuator to move said shaft to engage said anchor in said sleeve to move said anchor out a free end of said sleeve.

3. A method for inserting a bone anchor in a bore in a bone, the method comprising the steps of:

providing a bone anchor inserter comprising:
a handle;
a sleeve extending from said handle and having an opening in a side wall thereof;
a shaft slidably disposed in said sleeve; and
an actuator operative from said handle to move said shaft axially in said sleeve;

inserting a bone anchor through said opening and into said sleeve;

aligning a free end of said sleeve with said bore; and manipulating said actuator to move said shaft to engage said anchor in said sleeve to move said anchor out a free end of said sleeve and into said bore.

* * * * *